United States Patent
Lindstrom

(10) Patent No.: US 10,997,848 B2
(45) Date of Patent: May 4, 2021

(54) HYGIENE COMPLIANCE MONITORING

(71) Applicant: Essity Hygiene and Health Aktiebolag, Gothenburg (SE)

(72) Inventor: Hakan Lindstrom, Gothenburg (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 0 days.

(21) Appl. No.: 16/607,857

(22) PCT Filed: Apr. 27, 2017

(86) PCT No.: PCT/EP2017/060066
§ 371 (c)(1),
(2) Date: Oct. 24, 2019

(87) PCT Pub. No.: WO2018/196980
PCT Pub. Date: Nov. 1, 2018

(65) Prior Publication Data
US 2020/0193797 A1    Jun. 18, 2020

(51) Int. Cl.
*G08B 21/24*    (2006.01)

(52) U.S. Cl.
CPC ................. *G08B 21/245* (2013.01)

(58) Field of Classification Search
None
See application file for complete search history.

(56) References Cited

U.S. PATENT DOCUMENTS

| | | |
|---|---|---|
| 7,375,640 B1 | 5/2008 | Plost |
| 9,619,989 B1 | 4/2017 | Ewing et al. |
| 2007/0124393 A1 | 5/2007 | Maes |
| 2009/0273477 A1 | 11/2009 | Barnhill |
| 2010/0117836 A1 | 5/2010 | Seyed Momen et al. |

(Continued)

FOREIGN PATENT DOCUMENTS

| | | |
|---|---|---|
| CN | 101162531 A | 4/2008 |
| CN | 102257501 A | 11/2011 |

(Continued)

OTHER PUBLICATIONS

International Searching Authority, Search Report and Written Opinion issued in International Application No. PCT/EP2017/060065 dated Feb. 1, 2018 (14 pages).

(Continued)

*Primary Examiner* — John F Mortell
(74) *Attorney, Agent, or Firm* — Wood Herron & Evans LLP

(57) ABSTRACT

A system is provided for determining a hygiene compliance metric which indicates a usage of hygiene equipment. The system includes distributed hygiene equipment arranged to dispense a hygiene consumable and/or to dispose of a hygiene consumable, a tag configured to at least transmit radio signals; positioning equipment arranged to determine information on a position of said tag by at least receiving radio signals from said tag; and a processing entity. The processing entity is configured to receive said information on a position of said tag, to define a zone into which said tag may enter, to define a rule, and to calculate said hygiene compliance metric based on said information on the position, said zone, and said rule.

13 Claims, 4 Drawing Sheets

(56) References Cited

U.S. PATENT DOCUMENTS

| | | |
|---|---|---|
| 2010/0262430 A1 | 10/2010 | Gips et al. |
| 2011/0121974 A1 | 5/2011 | Tenarvitz et al. |
| 2013/0122807 A1* | 5/2013 | Tenarvitz ............. H04B 5/0031 455/41.1 |
| 2015/0254965 A1 | 9/2015 | Moore |
| 2019/0117809 A1* | 4/2019 | Katz .................. G06K 9/00201 |

FOREIGN PATENT DOCUMENTS

| | | |
|---|---|---|
| CN | 102497798 A | 6/2012 |
| CN | 105264535 A | 1/2016 |
| CN | 106154902 A | 11/2016 |
| CN | 106233352 A | 12/2016 |
| RU | 2007124393 A | 1/2009 |
| RU | 2014105114 A | 9/2015 |
| WO | 2009117662 A1 | 9/2009 |
| WO | 2011149884 A2 | 12/2011 |
| WO | 2014131074 A1 | 9/2014 |
| WO | 2016207370 A1 | 12/2016 |
| WO | 2018196979 A1 | 11/2018 |
| WO | 2018197023 A1 | 11/2018 |

OTHER PUBLICATIONS

International Searching Authority, Search Report and Written Opinion issued in International Application No. PCT/EP2017/060066 dated Feb. 1, 2018 (15 pages).

Russian Patent Office; Office Action in related Russian Patent Application No. 2019133593 dated Sep. 18, 2020; 10 pages.

National Intellectual Property Administration (CNIPA) of the Peoples Republic of China, First Office Action and Search Report in related applicaiton No. CN 201780090019.1, dated Oct. 12, 2020 (with English Translation), 18 pages.

\* cited by examiner

Fig. 3
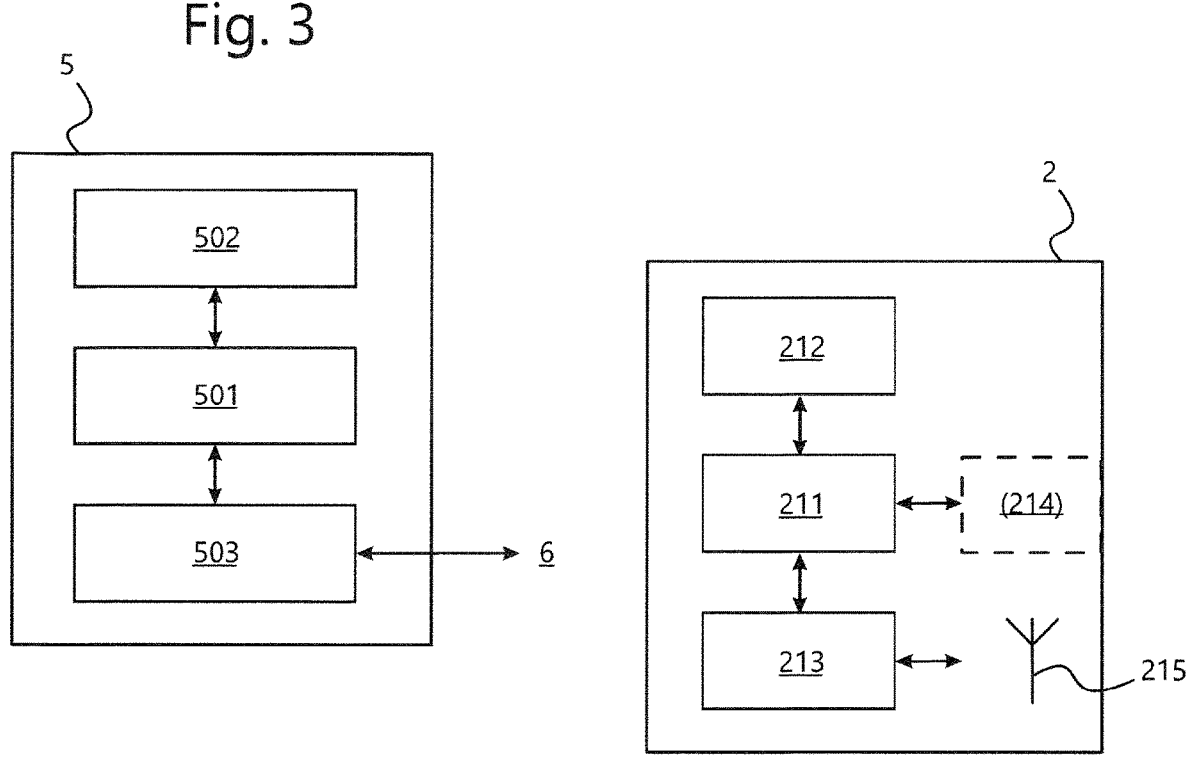
Fig. 4A
Fig. 4B
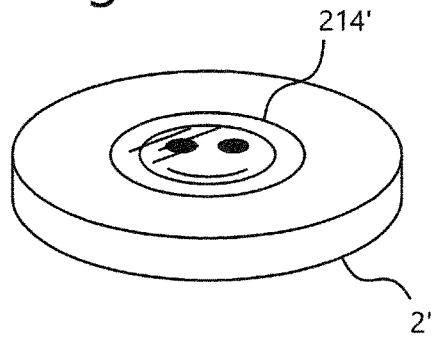
Fig. 4C
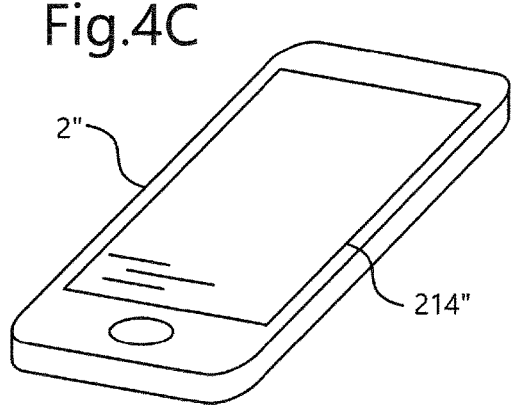

HYGIENE COMPLIANCE MONITORING

CROSS-REFERENCE TO RELATED APPLICATION

This application is a national phase entry of, and claims priority to, International Application No. PCT/EP2017/060066, filed Apr. 27, 2017, with the same title as listed above. The above-mentioned patent application is incorporated herein by reference in its entirety.

TECHNICAL FIELD

This application generally relates to determining a compliance indicator or metric in the context of hygiene equipment, such as soap, disinfectant, towel dispensers, and the like. For example, the application relates to determining a hygiene compliance indicator by tracking the use of hygiene equipment and observing movement and/or behavior of individuals (users) who are supposed to use hygiene equipment at specific instances and/or according to applicable rules.

BACKGROUND

Hygiene equipment is commonplace today in many facilities, such as hospitals, medical service centers, intensive care units, day clinics, private practices, lavatories, rest rooms, hotels, restaurants, cafes, food service places, schools, kindergartens, manufacturing sites, administration and office buildings, and, in general, places and facilities that are accessible to the public or to a considerable number of individuals. The mentioned hygiene equipment thereby includes various types of individual devices and installations such as soap dispensers, dispensers for disinfectant solutions, gels or substances, towel dispensers, glove dispensers, tissue dispensers, hand dryers, sinks, radiation assisted disinfectant points, ultraviolet (UV) light, and the like.

Although such hygiene equipment is commonplace today in many places, the use thereof by the individuals visiting these places or working in these places is still oftentimes not satisfactory. For example, hospitals, and, in general, medical service centers often suffer from hygiene deficiencies, which, in turn, may lead to the spread of infections and related diseases. In particular, such insufficient hygiene amongst medical care personnel coming into close contact with patients and bodily fluids can lead to the spread of infectious diseases amongst the personnel and other patients. It is also known that infections by highly resistant bacteria pose a severe problem in such places, especially in hospitals. In general, so-called Healthcare Associated Infections (HAI) are a real and tangible global problem in today's healthcare. HAI can be found to be currently the primary cause of death for 140,000 patients/year, affecting millions more and costs society in the range of billions of dollars per year.

At the same time, however, it is known that hygiene, and, in particular, hand hygiene, is an important factor as far as the spread of infectious diseases are concerned. Specifically, medical care personnel should make proper use of hand hygiene as often as possible so that the spread of bacteria and other disease causing substances is minimized. The actual usage of such hygiene equipment, however, may depend on—amongst others—the management of the facility, accessibility and usability of the equipment, culture, the cooperation and will exercised by the individuals working in these places or visiting such places, training of individuals, time pressure and possibly also other factors. In other words, an important factor remains the fact that individuals may not make use of installed and provided hygiene equipment although they are supposed to. Furthermore, it is generally accepted that an increased use of hygiene equipment can substantially contribute in reducing the spread of bacteria and the like, which, in turn, can drastically reduce the appearance of related infections and diseases.

For example, a corresponding relatively "low" compliance may indicate that the actual use of hygiene equipment is not satisfactory, whilst relatively "high" compliance may indicate that the actual use of hygiene equipment corresponds, within a given threshold, to some target usage, and, consequently, may be regarded as being satisfactory. A tangible figure for estimating the quality of hygiene compliance may be found in a so-called compliance metric that as such may provide many advantages, since it can give a concise picture to operators of the corresponding facility so that they may initiate measures for increasing and promoting the actual use of hygiene equipment.

Therefore, there are already ways of measuring and/or estimating such a compliance metric in the arts, wherein the conventional approaches usually rely on measuring and/or observe "manually" by a human observer so-called opportunities and comparing these obtained opportunities to a measured/detected/observed actual use of the hygiene equipment. In other words, the opportunities indicate any event when hygiene equipment should or could have been used. By then comparing this "should/could"-value to an actual usage value a compliance metric can be calculated, as e.g. a percentage value or a ratio. In general, the opportunities can be well defined figures, since they may be associated to specific rules and/or recommendations. For example, the World Health Organization (WHO) has defined a so-called "Five Moments Of Hand Hygiene" including as explicit definitions for opportunities: 1. Before patient contact; 2. Before aseptic task; 3. After body fluid exposure risk; 4. After patient contact; and 5. After contact with patient surroundings.

Besides manually measuring opportunities and detecting the usage of hygiene equipment there exist also fully automated systems, where opportunities are detected by tags carried by an individual subject to hygiene compliance and associated equipment for detecting when a tag moves into a given vicinity as, for example, taught by U.S. Patent Publication No. 2013/0027199. The latter may define a zone, for example around a patient's bed that requires the use of hygiene equipment before entering and/or after leaving the zone. For example, having not used hygiene equipment before entering a zone around a patient's bed may indicate non-compliance, whilst having used hygiene equipment before entering the zone and after leaving the zone may indicate compliance.

However, the mentioned arts determine the metrics on hygiene compliance by conventional ranging, locating, and tracking techniques that are not specifically adapted to the applicable preconditions and do not take into account the characteristic circumstances of tracking devices and/or individuals in the context of hygiene compliance. In particular, technologies such as satellite based positioning systems (e.g. Global Positioning System (GPS), Galileo, GLONASS, WAAS, etc.) and mobile network locating services (via GSM, PCS, DCS, GPRS, UMTS, 3GPP, LTE, etc.) have only a limited accuracy and availability indoors, where most of the tracking may occur in the context of determining a hygiene compliance. Similarly, conventional indoor techniques, such as employing a received signal strength (RSS) provide firstly only a limited accuracy and, secondly, are susceptible to interference with other radio signal sources, including the ubiquitous mobile phone and wireless LAN networks and installations. At the same time, a sufficient accuracy can be vital for a system so that it produces a reliable figure on the hygiene compliance. Specifically, the required precision may relate to the "human scale", i.e. in many cases an "arm-length" that usually translates to below 1 m and preferably below 50 cm.

Thus, it would be desirable to provide improved concepts of determining a hygiene compliance in connection with the actual and appropriate use of distributed hygiene equipment. Equally there is a need for improved equipment that determines a hygiene compliance and conveys corresponding information to appropriate addressees for ultimately encouraging the actual use hygiene equipment.

SUMMARY

To address these and other problems with conventional designs, according to an embodiment of the present invention there is provided a system for determining a hygiene compliance metric which indicates a usage of hygiene equipment. The system includes distributed hygiene equipment arranged to dispense a hygiene consumable and/or to dispose of a hygiene consumable and a tag configured to at least transmit radio signals. The system further includes positioning equipment arranged to determine information on a position of the tag by at least receiving radio signals from the tag, and configured to determine information on a direction along which a radio signal was received from the tag for determining the information on a position. The system also includes a processing entity which is configured to receive the information on a position of the tag, to define a zone into which the tag may enter, to define a rule, and to calculate the hygiene compliance metric based on the information on the position, the zone, and the rule.

According to another embodiment, there is provided a method for determining a hygiene compliance metric which indicates a usage of hygiene equipment. The method includes detecting a usage instance of distributed hygiene equipment arranged to dispense a hygiene consumable and/or to dispose of a hygiene consumable; at least transmitting a radio signal from a tag; determining information on a position of the tag by at least receiving radio signals from the tag and by determining information on a direction along which a radio signal was received from the tag; receiving the information on a position of the tag; defining a zone into which the tag may enter; defining a rule, and calculating the hygiene compliance metric based on the information on the position, the zone, and the rule.

BRIEF DESCRIPTION OF THE DRAWINGS

Various additional features and advantages of the invention will become more apparent to those of ordinary skill in the art upon review of the following detailed description of one or more illustrative embodiments taken in conjunction with the accompanying drawings. The accompanying drawings, which are incorporated in and constitute a part of this specification, illustrate one or more embodiments of the invention and, together with the general description given above and the detailed description given below, explain the one or more embodiments of the invention.

FIG. 3 is a schematic view of a processing entity used with the system according to an embodiment of the present invention.

FIG. 4A is a schematic view of a tag from a functional point of view, the tag being usable with the system according to embodiments of the present invention.

FIG. 4B is a top perspective view of a tag in the form of compact electronic device, in accordance with another embodiment.

FIG. 4C is a top perspective view of a tag in the form of a smartphone or similar device, according to another embodiment.

DETAILED DESCRIPTION

Figure 1:
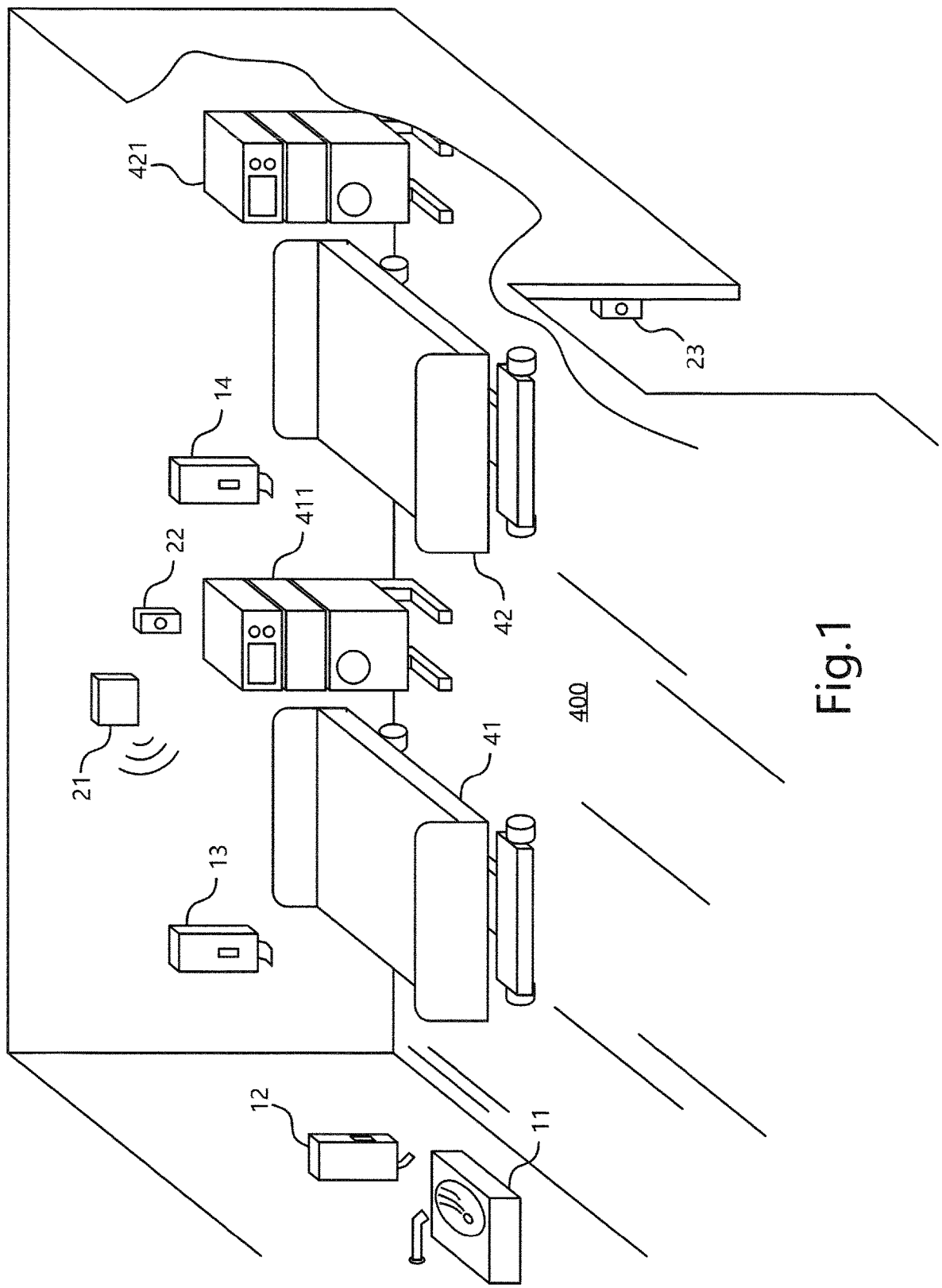
FIG. 1 is a schematic view of a typical environment where the actual usage of hygiene equipment is subject to compliance, which may be used with one embodiment.

FIG. 1 shows a schematic view of a typical environment where the actual usage of hygiene equipment is subject to compliance, and where the individuals are usually encouraged to use the hygiene equipment at specific instances. As an example, there is shown as a facility an intensive care unit 400 with corresponding intensive care points: first and second patient stations 41, 42 and first and second patient care equipment 411, 421. As can be seen, the intensive care unit 400 may be occupied by one or two patients in the shown configuration, whilst the embodiments of the present invention may envisage also other intensive care units with any number of patients and personnel and/or other facilities as mentioned elsewhere in the present disclosure. Examples for other possible working environments include hospitals and medical service centers in general, day clinics, private practices, lavatories, rest rooms, hotels, restaurants, cafes, food service places, schools, kindergartens, manufacturing sites, administration and office buildings, and, in broad terms, places and facilities that are accessible to the public or to a considerable number of individuals.

The configuration shown in FIG. 1 can acquire data indicating the usage of the hygiene equipment from equipment sensor arrangement provided for or in one or more of the individual pieces of hygiene equipment, such as a washing sink 11, a soap dispenser 12, and a first and a second disinfectant dispenser 13, 14. In this way, the system is able to receive usage data from these pieces of equipment 11-14 as possibly individual signals from each corresponding device/sensor. Other examples of hygiene equipment may include a towel dispenser, an alcogel dispenser, a tissue dispenser, a hygiene article dispenser, a waste bin, a used towel bin, and a toilet paper dispenser. Likewise, opportunities can be detected by corresponding sensors including a vicinity sensor 21, a light barrier sensor 22 and a door passing sensor 23. As already mentioned earlier, the data on the usage and on the opportunities can be collected and processed for calculating a hygiene compliance metric or indicator, which, in turn, indicated to what degree the individuals (e.g. nurses, doctors, and caretakers) use the hygiene equipment at appropriate opportunities.

Normally, the data generated by the distributed equipment 11, 12, 13, 14, 21, 22, and 23 is retrieved by some kind of central data processing and storage entity (not shown, e.g. a server), where the hygiene compliance metric is calculated. However, the calculated hygiene metric can only be as accurate as are the corresponding basis data. For example, an inaccurate positioning of an individual may result in determining an opportunity for using hygiene equipment when actually opportunity existed. As a result, the individual may be attributed wrongly with achieving only a low compliance contribution. A door passage sensor 23 by itself may not be able to monitor movement between the beds 41 42, thus not detecting potential for patient cross-contamination. Such inaccurate data acquisition may lead to an inaccurate estimation of the compliance which may then be perceived negatively by the individuals, and, eventually, such circumstances may result in a decreased acceptance of the system so that the ultimate goal of promoting the use of hygiene equipment by the individuals may be missed. Naturally, also the reverse case can happen that the calculated metric suggests good hygiene compliance while it is actually not.

Figure 2:
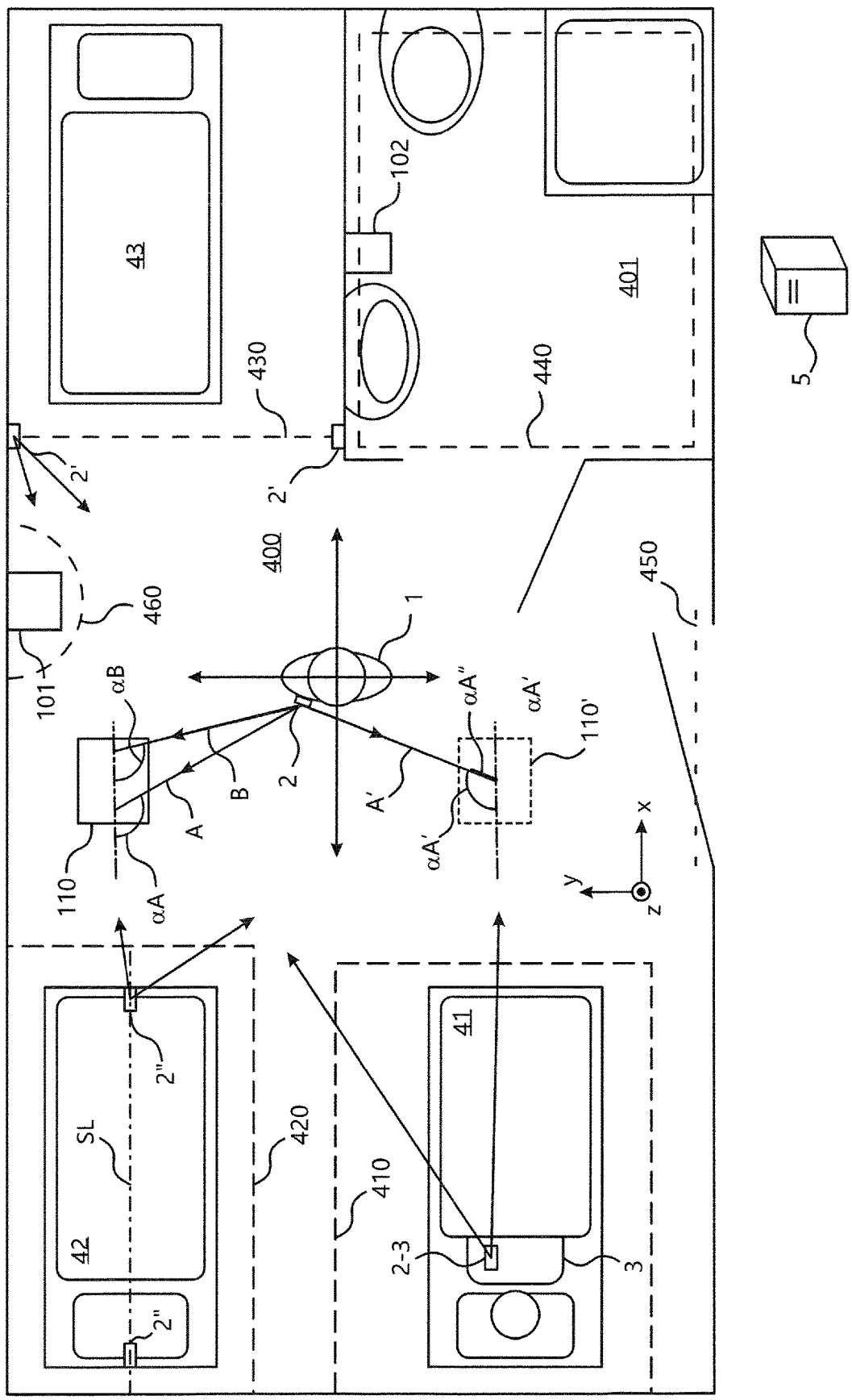
FIG. 2 is a schematic view of a deployment of a system according to an embodiment of the present invention into an environment similar to the one shown in FIG. 1.

FIG. 2 shows a schematic view of a deployment of a system according to an embodiment of the present invention. Specifically, the deployment is explained again along an example of a hospital environment, which is seen from atop and comprises patient stations (beds) 41 (with patient 3), 42, and 43. An individual 1, e.g. a doctor, a nurse, a member of personnel, another patient or a visitor, can move freely in the ward 400 for fulfilling any given task(s). The individual 1 carries a tag 2 which is explained in greater detail elsewhere in the present disclosure.

For example, the individual 1 may be assumed to have visited the restroom/bathroom 401 and is now heading toward a patient lying in patient station 42. A compliance rule may require that an individual 1 uses hygiene equipment (e.g. a soap dispenser 102) before leaving a restroom such as bathroom 401 having a shower, a toilet, and a hand wash basin. A "compliant" individual 1 may wash his/her hands and may use the soap dispenser 102. This piece of hygiene equipment 102 may be configured to detect the usage instance and send out a signal over a wired or wireless interface and via some kind of network to a central data processing and storage entity (e.g. a server).

Generally, an embodiment of the present invention is a system for determining a hygiene compliance metric which indicates a usage of hygiene equipment. The system as shown may comprise firstly distributed hygiene equipment that is arranged to dispense a hygiene consumable and/or to dispose of a hygiene consumable, and that is arranged to detect a usage instance indicating a use of the hygiene equipment by a user, and to send information on the usage instance toward a processing entity. As mentioned, the individual 1 may use the soap dispenser 102 as one exemplary form of a piece of hygiene equipment, and this detected usage can be forwarded to a (remote) server 5 as a form of the processing entity. The mentioned tag 2 can be likewise part of the system and can be configured to at least transmit radio signals and can be arranged to be carried by the individual 1, i.e. a user. The tag 2, just as the individual 1, can move in the ward basically in the three dimensions x, y, and z, wherein the z-direction is assumed to coincide with the vertical direction and thus to be perpendicular to the drawing plane.

The system further comprises positioning equipment that is arranged to determine information on a position of a tag by at least receiving radio signals from it, and that is configured to determine information on a direction along which a radio signal was received from the tag. In one embodiment, the positioning equipment is arranged to determine the information on a received direction based on determining an angle of arrival of a received radio signal. Preferably, the information on the received direction is determined based on determining at least two angles of arrival of a received radio signal and information indicating a vertical height of a tag, i.e. information that indicates the recent or usual height of tag 2 as the radio signal source in the z-direction. This information can then be employed for determining information on a position of the tag, and, in turn, of the individual. As shown, there is a positioning device 110, for example mounted on or in the ceiling of the ward 400. This device 110 can receive a radio signal from tag 2 e.g. via two different paths A and B. This would result in two detectable angles of arrival angle $\alpha A$ and $\alpha B$ at the site of the device 110.

Corresponding information can be forwarded to server 5 or also locally, i.e. in the device 110, processed to determine information on a position of tag 2. This processing may consider further measured or assumed information so as to determine a location of tag 2. For example, the carrying height in the z-direction may be further measured or assumed. In the latter case, this may be accomplished by affixing the tag 2 to the individual at a known height. This height may be known to the server 5 or may also be made known to tag 2 so that it can convey corresponding information as payload data to a radio signal A, B, or A'. In this case the tag 2 may comprise means to configure the actual height and means for generating corresponding payload data and radio signals.

As an alternative or in addition to the above, the position of a tag can be determined based on information on a direction along which radio signal A' is received as explained in conjunction with the positioning device 110'. In particular, this solution considers the direction of arrival of the radio signal A' in relation to an angle $\alpha A'$ in the x-y-plane and an angle $\alpha A''$ in the x-z- or y-z-plane. Again, the information on the direction of arrival with information on the angles $\alpha A'$ and $\alpha A''$ together with information on the height in the z-direction allows the device 110' or the server 5 to calculate information on the position of the tag 2. In general, however, the devices 110 and 110', or two or more devices of the same type can be combined so as to achieve an overall improved accuracy of any location/position information.

The system further comprises server 5 as a processing entity. This server is configured to receive the information on the usage instance, to receive the information on a position of the tag, to define a zone into which the tag may enter, to define a rule, and to calculate the hygiene compliance metric based on the information on the usage instance, information on the position, the zone, and the rule.

Specifically, the mentioned zones may be defined in terms of "virtual" zones around beds, rooms, hygiene equipment, and any other objects and positions which generally relate to a usage of hygiene equipment and/or an opportunity in relation with the use of hygiene equipment. In this way, zones 410, 420, and 430 may be defined for, respectively, beds or patient stations 41, 42, and 43. Likewise, a zone 440 may be defined for the bathroom 401, and the zones can also be determined in terms of lines 450 and 430 that may be seen as singular zone boundaries. In particular, crossing a line 450 or 430 may result in a determination of entering or leaving a zone whilst the remaining boundaries of the zones are not, or do not need to be defined (e.g. like in the case of the patient station 43 in the corner of room 400). In any way, such zones may define opportunities, in the sense that a tag 2 entering such a zone indicates to the system that the individual carrying tag 2 was supposed or is now supposed to use hygiene equipment.

Similarly, a zone may also be defined for determining a usage event. As for example shown around dispenser 101 there is defined an associated zone 460. Entering this zone may be interpreted as an individual carrying a tag uses the hygiene equipment. In this way, the information on the usage instance is received in terms of information on a position of a tag in connection with a specific zone—here zone 460 around dispenser 101. Generally, the server 5 may receive this information and consider one or more rules that then allows it to calculate the hygiene compliance metric based on the information on the usage instance, and the information on the position in connection with at least one zone.

As far as the zones as such is concerned, different schemes may be adopted for their respective definition. Firstly, a zone may be a purely "virtual" zone such as zone 440, which can be defined by respective information, for example, in the server 5. In this way, the processing of server 5 may determine whether a tag 2 enters or leaves the zone 440 by receiving information from the positioning device 110/110' and calculating a position of tag 2 in relation to the zone 440. Likewise, a zone may also be defined "locally" and/or dynamically by respective tags 2', 2", and 2-3.

For example, tags 2' may be configured to define corners of a zone or borderline. As can be seen in FIG. 2, the system may define a zone or borderline 430 by locating tags 2' with device 110 or 110'. The radio signals emitted from tags 2' may carry payload which can identify their respective association to one another and/or information on a type of zone (e.g. borderline, rectangle zone with dimensions and further positional data/definitions relative to the tags' positions). Similarly, tags 2" may be arranged along a symmetry line SL of bed 42. According information may be conveyed toward or may be present in server 5 so as to define zone 420.

A further embodiment considers the definition of a moving or dynamic zone. For example, patient 3 is provided with a tag 2-3 that defines a zone 410 around patient 3 regardless of his/her current position. This allows determining correct compliance regardless of whether the target is mobile and is thus able to move outside to an otherwise fixedly defined zone. Likewise, a tag 2-3 could also be affixed to a bed, to a specific point in a room or to a piece of equipment (medical devices, cleaning trolley, etc.). In all, the definition of zones by tags may provide the advantages of easy definition of zones, dynamic definition of zones, easy modification and deactivation/activation of zones. For example, tags can be provided with a simple user interface (switch, sensor, LED, LCD, etc.) so as to allow an on-the-spot activation/deactivation. The system may thus in some embodiments be able to consider zones only when they are actually "hot" in the sense that—for example—a bed is indeed occupied.

Any zone can be generally defined on a "human scale" taking the measurements of the human body as the reference. A width of a zone around a bed may therefore be slightly more than arm's length, so as to be in the range of 50 cm to 100 cm, implying that a person outside this zone can be assumed to have no chance of touching the patient in the bed whereas the same person inside the zone at least has a theoretical possibility to touch the patient and is therefore subject to hand hygiene regulations, and, in turn, hand hygiene compliance observation.

The individual 1 may then proceed toward patient station 42. A further compliance rule may require that individual 1 uses hygiene equipment (e.g. a disinfectant dispenser 101) before coming into contact with the patient at station 42. Here, the determination of the usage and the opportunity may be vicinity or location based in connection with zone 460. Similarly, the (corresponding) opportunity may be determined based on a location relative to the target, in this case the patient station 42. Specifically, server 5 may define the zone 420 and consider a tag entering the zone 420 as an instance of an opportunity to now use or to have briefly before used hygiene equipment. This determination may be simply based on the assumption that an individual carrying tag 2 and entering zone 420 will also get in close or physical contact with the patient and/or the surroundings.

This is the very reason, why an opportunity is associated with a usage instance, since the physical contact to patient should be preceded by using hygiene equipment in order to minimize the spread of potentially infectious bacteria, viruses, fungi, etc. Likewise, also the physical contact with a patient may be associated with a usage of hygiene equipment thereafter in order not carry anything infectious from that patient to others. Having the information on a hygiene compliance metric at hand may now allow a feedback sequence for conveying information on the achieved hygiene compliance to the users/individuals. For this purpose, the server 5 may be employed to retrieve and analyze the information and to take any suitable and desired feedback actions so that the use of hygiene equipment by the individuals is actually encouraged.

FIG. 3 shows a schematic view of a processing entity according to an embodiment of the present invention. Specifically, the processing entity 5 can be in the form of a server or personal computer, or, more generally, in the form of processing resources of a cluster or datacenter. The processing entity 5 may be part of a system for determining a hygiene compliance metric which indicates a usage of hygiene equipment. For this purpose, the server entity 5 may comprise or may have access to processing resources 501, memory resources 502 and communication resources 503, where the latter establish a communication path via one or more networks 6 toward distributed hygiene equipment, a tag, and/or positioning equipment. In this way, entity 5 can receive information on a usage instance from the hygiene equipment, determine information on an angle along which a radio signal was received from a tag, and/or information on a position of the tag.

This and other functionalities may be implemented as code stored in the memory resources 502 that can instruct the processing resources (or circuit) to receive and process the data in connection with information on the usage instance and with information on the position of a tag. The code may further implement a definition of one or more zone into which the tag may enter, to define one or more rules, and to calculate the hygiene compliance metric based on the information on the usage instance, information on the position, the zone, and the rule.

As regards the mentioned rules, a determination of an opportunity (e.g. entering of a bed zone) without a prior usage determination will indicate non-compliance, just as an elapse of a time span after a determined opportunity (e.g. entering of a room) without an associated usage determined. In general, a determined usage or opportunity may be internally handled by the processing resources 501 as a data record carrying type and association information. For example the association information of an opportunity record can store information on an associated type of usage record. If a corresponding pair is determined within a corresponding time span the processing resources 501 may determine compliance and accordingly set an compliance indicator or a contribution to a metric to a corresponding value, e.g. "1". Likewise, if no corresponding pair is determined within a time span the processing unit 211 may determine non-compliance and accordingly set the indicator/contribution to a corresponding non-compliance value, e.g. "0".

An alternative mechanism would involve the storing and processing of vector in the form of, for example, [usage opportunity], where a compliance indicator indicating compliance could be obtained for [1 1], whereas a compliance indicator indicating non-compliance could be obtained for [1 0] or [0 1]. This mechanism may add flexibility in analysis as well as the possibility to also consider metadata in an easy manner. For example, additional values x, y, . . . may be considered as [usage compliance x y . . . ] for expressing compliance to additional rules relating to, for example, a time, a position, a user ID, and the like. In general, however, the mentioned metadata may naturally also be considered by the above mentioned data records in the form of additional fields.

FIGS. 4A to 4C show schematic views of deployments of tags according to respective embodiments of the present invention. FIG. 4A shows a schematic of a tag 2 from a functional point of view. The tag 2 is generally adapted to be carried by the user and comprises a radio unit 213 that is configured to at least transmit radio signals via an antenna 215, and a processing unit 211, and—optionally—an operation/notification unit 214. The tag 2 may further comprise a memory unit 212 that may store code for instruction the processing unit 211 to implement any desired functionality. However, the configuration may well be integrated into the processing unit 211 itself, so that no separate or individual memory unit 212 is necessary. The radio unit 213 may employ any suitable technology and protocols and preferred technologies include Bluetooth, WiFi, WLAN, WiMAX, UWB (Ultra wide band), and the like.

The processing unit 211 is generally configured, for example by respective programming, to instruct the radio unit 213 to transmit radio signals that can be received by positioning equipment in order to determine information on a position of tag 2. Further, the operation/notification unit 214 may be employed to operate the tag as such (e.g. configuration, set and modify settings, etc.) or to convey information to the user in accordance with the determined hygiene compliance. In this way, it is possible to provide an individual immediately with a feedback on a good compliance or non-satisfactory behavior. Furthermore, the tag 2 can assist in collecting any desired information and can even also carry out positioning by determining and processing information on an angle of arrival (see also the description in conjunction with FIG. 2).

FIG. 4B shows a schematic of a tag 2' in the form of compact electronic device. The tag 2' will internally comprise all the necessary functional features as described above in conjunction with FIG. 4A. In this embodiment, however, the operation/notification unit at least comprises a display 214', optionally a touch-sensitive display, which can be instructed also, for example, to display a positive emoticon in case of determining compliance. A negative emoticon may be displayed for conveying a non-compliance to the user. This display may be accompanied by any acoustic and/or vibrational signal in order to make the user aware of the feedback also in situations where the tag 2' is carried inside a pocket or not in the immediate visible range of the user (e.g. attached to a shirt).

FIG. 4C shows a schematic of a tag 2" in the form of a smartphone or similar electronic device. The device defining the tag 2" will internally comprise all the necessary functional features as described above in conjunction with FIG. 4A. In this embodiment, however, the operation/notification unit at least comprises the device's display 214" which can be instructed to display any content for indicating compliance and non-compliance. It should be clear that the functionalities may be implemented by a program or application ("app") which instructs the device's resources as a form of radio unit, a notification unit, and a processing unit. Again, any display may be accompanied by any acoustic and/or vibrational signal in order to make the user aware of the feedback also in situations where the device is outside the immediate visible range for the user.

Figure 5A:
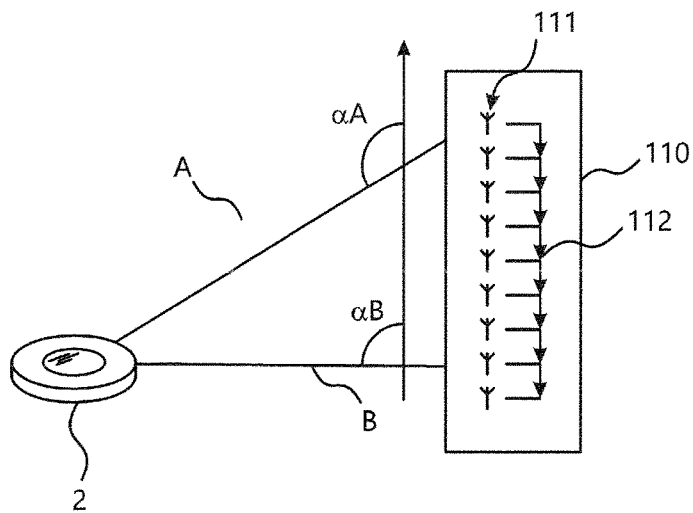
FIG. 5A is a schematic view of positioning equipment for determining information on a direction or an angle of arrival according to one embodiment.

FIG. 5A shows a schematic view of positioning equipment for determining information on a direction or an angle of arrival according to an embodiment of the present invention. Specifically, it is shown a possible implementation of the positioning device 110 which provides in this embodiment an antenna array 111 and a phase run time line 112. A tag 2 is assumed to emit a radio signal that then can reach the positioning device 110, and, with this, the antenna array 111 along two paths A and B along the line of sight. These paths will intersect a given base line with corresponding angles αA and αB. It is known to determine information on a distance and/or a position with two, three or more angles available. This concept is known as triangulation and methods exist in the arts.

The angles αA and αB can be for example determined by the phase run time line 112 where signals received by the individual antennas run and establish a certain phase relation to each other. This phase relation is a figure for a timing difference with regard to points in time when the radio signal has hit the antennas along the different paths. With this information angles can be obtained, which can serve as a basis for determining the information on a position and/or distance. Likewise, a series of arrival times over the antenna array can be measured from which then one or more angles, and, in turn, an information on a position of the originator of the radio signal can be calculated.

Figure 5B:
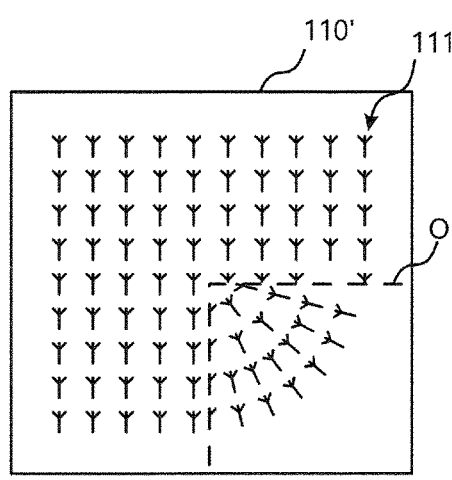
FIG. 5B is a schematic view of positioning equipment for determining information on a direction or an angle of arrival according to another embodiment.

FIG. 5B shows a schematic view of positioning equipment for determining information on a direction or an angle of arrival according to another embodiment of the present invention. This alternative embodiment considers the device 110' arranged to measure information on an angle αA' in the x-y-plane and an angle αA" in the x-z- or y-z-plane. Specifically, this embodiment considers an array of antennas 111 in the form of a two-dimensional matrix (as shown) or a circular matrix with antennae arranged along polar coordinates as shown in the option box 0. An incoming radio signal will trigger the individual antennae of the matrix at different times and thus allows the calculation of the two angles αA' and αA" for, ultimately, determining information on a position in 2 or 3 dimensions of a radio signal source (i.e. a tag). Further, a spherical antenna may be employed that provides the individual antennae on a surface of a sphere.

Figure 6:
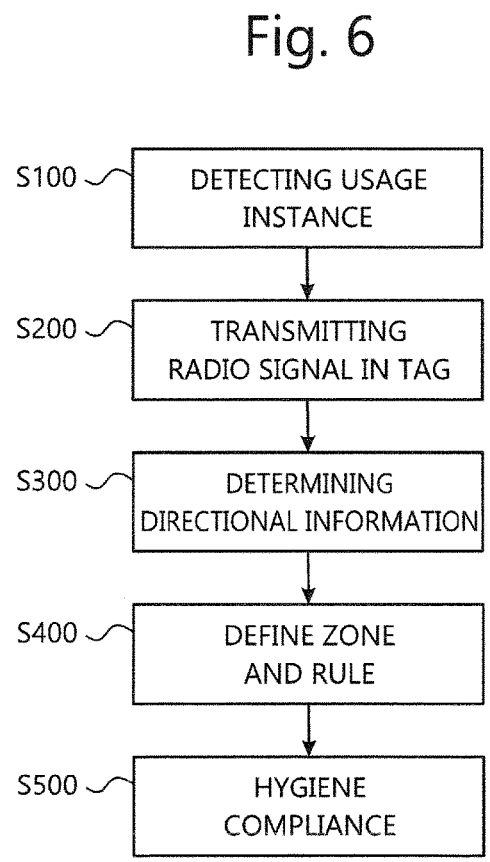
FIG. 6 is a flowchart of one embodiment of a method according to the present invention.

FIG. 6 shows a flowchart of a general method embodiment of the present invention. According to this embodiment of the present invention a method is provided for determining a hygiene compliance metric which indicates a usage of hygiene equipment, comprising a step S100 of detecting a usage instance indicating a use of distributed hygiene equipment by a user, the hygiene equipment arranged to dispense a hygiene consumable and/or to dispose of a hygiene consumable; a step S200 of transmitting radio signals from a tag; a step S300 of determining information on a position of the tag by at least receiving radio signals from the tag, and determining information on a direction along which a radio signal was received from the tag for determining the information on a position; receiving the information on a position of the tag; a step S400 of defining a zone into which the tag may enter and defining a rule; and a step S500 calculating the hygiene compliance metric based on the information on the position, the zone, and the rule.

It is noted that the above sequence can be modified and is not to be seen as requiring a specific order. For example, S400 can be carried out before any other steps or, in general, at least before performing step S500. Likewise, the order of information retrieval concerning the usage and opportunities may be reversed or the corresponding information can be obtained concurrently and continuously.

Although detailed embodiments have been described, these only serve to provide a better understanding of the invention and are not to be seen as limiting.

To this end, the embodiments described above are only descriptions of preferred embodiments of the present invention, and do not intended to limit the scope of the present invention. Various variations and modifications can be made to the technical solution of the present invention by those of ordinary skills in the art, without departing from the design and spirit of the present invention. The variations and modifications should all fall within the claimed scope defined by the claims of the present invention.

What is claimed is:

1. A system for determining a hygiene compliance metric which indicates a usage of hygiene equipment, the system comprising:

distributed hygiene equipment arranged to dispense a hygiene consumable and/or to dispose of a hygiene consumable;

a tag configured to at least transmit radio signals;

positioning equipment arranged to determine information on a position of the tag by at least receiving radio signals from the tag, and configured to determine information on a direction along which a radio signal was received from the tag for determining the information on the position; and a processing entity which is configured to receive the information on the position of the tag, to define a zone into which the tag may enter, to define a rule, and to calculate the hygiene compliance metric based on the information on the position, the zone, and the rule, wherein the processing entity defining the zone into which the tag may enter includes defining one or more usage zones each surrounding a piece of the distributed hygiene equipment and defining one or more opportunity zones surrounding persons or locations where hygiene consumable use is desired before or after interaction with such persons or locations, and wherein each of the usage zones and each of the opportunity zones is defined by sizing on a human scale to reliably confirm interaction with the distributed hygiene equipment or the persons or locations where hygiene consumable use is desired, wherein the tag is carried by a user and the processing entity processes the information on the position of the tag in relation to one of the usage zones for determining a usage instance of a piece of the distributed hygiene equipment, and in relation to one of the opportunity zones for determining an opportunity in relation to a usage instance for, in turn, having the processing entity calculate the hygiene compliance metric based on a sequence of positions of the tag to determine for each such opportunity whether a usage instance within a time window before or after the opportunity has occurred at any of the usage zones and can be paired with the opportunity to indicate compliance with desired hygiene practices.

2. The system of claim 1, wherein the positioning equipment is arranged to determine the information on a received direction based on determining an angle of arrival of a received radio signal.

3. The system of claim 2, wherein the positioning equipment is arranged to determine the information on a received direction based on determining at least two angles of arrival of a received radio signal and information indicating a vertical height of a tag.

4. The system of claim 1, wherein another tag is arranged to be associated with a piece of the distributed hygiene equipment and the processing entity is configured to define one of the usage zones in relation to a position of the tag associated with the piece of the distributed hygiene equipment, the one of the usage zones being associated with a usage instance of the piece of the distributed hygiene equipment.

5. The system of claim 1, wherein another tag is arranged to be associated with an object or individual where hygiene consumable use is desired before or after interaction with the object or individual, and the processing entity is configured to define one of the opportunity zones in relation to a position of the tag associated with the object or individual, the one of the opportunity zones being associated with an opportunity in relation to a usage instance of the piece of distributed hygiene equipment.

6. The system of claim 1, wherein at least a piece of the distributed hygiene equipment is arranged to detect the usage instance indicating a use of the piece of the distributed hygiene equipment by a user, and to send information on the usage instance toward the processing entity.

7. The system of claim 1, wherein the processing entity is configured to process information on a type of event received as payload data from a radio signal from the tag, the type of event including an opportunity and/or a usage instance.

8. The system of claim 1, wherein the processing entity is configured to process data records comprising information on a type of usage and/or opportunity and information on an association to another record for determining the hygiene compliance metric.

9. The system of claim 1, wherein the processing entity is configured to consider a time between a determination of a usage instance and a determination of an opportunity for determining the hygiene compliance metric.

10. The system of claim 1, wherein the processing entity is configured to store information on several hygiene compliance indicators, each indicator relating to at least one determined usage instance and one determined opportunity.

11. The system of claim 1, wherein a piece of the distributed hygiene equipment is any one of a soap dispenser, a towel dispenser, a disinfectant dispenser, an alcogel dispenser, a tissue dispenser, a hygiene article dispenser, a waste bin, a used towel bin, and a toilet paper dispenser.

12. The system of claim 3, wherein another tag is arranged to be associated with a piece of the distributed hygiene equipment and the processing entity is configured to define one of the usage zones in relation to a position of the tag associated with the piece of the distributed hygiene equipment, the one of the usage zones being associated with the usage instance of the piece of the distributed hygiene equipment, wherein another tag is arranged to be associated with an object or individual where hygiene consumable use is desired before or after interaction with the object or individual, and the processing entity is configured to define one of the opportunity zones in relation to a position of the tag associated with the object or individual, the one of the opportunity zones being associated with an opportunity in relation to the usage instance of the piece of distributed hygiene equipment, wherein at least a piece of the distributed hygiene equipment is arranged to detect the usage instance indicating a use of the piece of the distributed hygiene equipment by a user, and to send information on the usage instance toward the processing entity, wherein the processing entity is configured to process information on a type of event received as payload data from a radio signal from the tag, the type of event including an opportunity and/or the usage instance, wherein the processing entity is configured to process data records comprising information on a type of usage and/or opportunity and information on an association to another record for determining the hygiene compliance metric, wherein the processing entity is configured to consider a time between a determination of the usage instance and a determination of an opportunity for determining the hygiene compliance metric, wherein the processing entity is configured to store information on several hygiene compliance indicators, each indicator relating to at least one determined usage instance and one determined opportunity, and wherein a piece of the distributed hygiene equipment is any one of a soap dispenser, a towel dispenser, a disinfectant dispenser, an alcogel dispenser, a tissue dispenser, a hygiene article dispenser, a waste bin, a used towel bin, and a toilet paper dispenser.

13. A method for determining a hygiene compliance metric which indicates a usage of hygiene equipment, comprising the steps of:

detecting a usage instance of distributed hygiene equipment arranged to dispense a hygiene consumable and/or to dispose of a hygiene consumable;

at least transmitting a radio signal from a tag being carried by a user;

determining information on a position of the tag by at least receiving radio signals from the tag and by determining information on a direction along which a radio signal was received from the tag;

receiving the information on a position of the tag;

defining a zone into which the tag may enter, specifically by defining one or more usage zones each surrounding a piece of the distributed hygiene equipment and one or more opportunity zones surrounding persons or locations where hygiene consumable use is desired before or after interaction with such persons or locations, each usage zone being defined for determining a usage instance of a piece of the distributed hygiene equipment, and each opportunity zone being defined for determining an opportunity in relation to a usage instance, wherein each of the usage zones and each of the opportunity zones is defined by sizing on a human scale to reliably confirm interaction with the distributed hygiene equipment or the persons or locations where hygiene consumable use is desired;

defining a rule, and calculating the hygiene compliance metric based on the information on the position, the usage zone, the opportunity zone, and the rule, such that the hygiene compliance metric is calculated on the basis of a sequence of positions of the tag to determine: one or more opportunities indicated by entry of the tag into opportunity zones, one or more usage instances indicated by entry of the tag into usage zones, and for each such opportunity whether a usage instance within a time window before or after the opportunity has occurred at any of the usage zones and can be paired with the opportunity to indicate compliance with desired hygiene practices.

* * * * *